United States Patent [19]

Huffman et al.

[11] Patent Number: 4,883,480
[45] Date of Patent: Nov. 28, 1989

[54] INFANT DIAPER WITH IMPROVED FIT

[75] Inventors: Gloria M. Huffman, Skillman; Heinz A. Pieniak, No. Brunswick, both of N.J.

[73] Assignee: McNeil-PPC, Inc., Milltown, N.J.

[21] Appl. No.: 296,992

[22] Filed: Jan. 17, 1989

Related U.S. Application Data

[63] Continuation of Ser. No. 42,501, Mar. 27, 1987, abandoned, which is a continuation-in-part of Ser. No. 838,878, Mar. 10, 1986, abandoned, which is a continuation of Ser. No. 641,666, Aug. 17, 1984, abandoned.

[51] Int. Cl.$^4$ .............................................. A61F 13/16
[52] U.S. Cl. .................................... 604/385.1; 604/378
[58] Field of Search .................... 604/385.1, 372, 378, 604/358, 375.2

[56] References Cited

U.S. PATENT DOCUMENTS

| | | | |
|---|---|---|---|
| 3,779,246 | 12/1973 | Mesek et al. | 604/366 |
| 4,253,461 | 3/1981 | Strickland et al. | 604/389 |
| 4,381,781 | 5/1983 | Sciaraffa et al. | 604/373 |
| 4,397,645 | 8/1983 | Buell | 604/380 |
| 4,610,682 | 9/1986 | Kopp | 604/385.1 |

Primary Examiner—Stephen C. Pellegrino
Attorney, Agent, or Firm—Robert L. Minier

[57] ABSTRACT

A disposable infant diaper is provided having a modified "T" configuration with a substantially rectangular absorbent core making the stem of the "T" and breathable fabric making the top of the "T". The breathable fabric is substantially non-yielding in a cross-direction. The closure means are integral inside the top of the "T" which forms the back waistband portion.

1 Claim, 2 Drawing Sheets

INFANT DIAPER WITH IMPROVED FIT

This is a continuation patent application of application Ser. No. 042,501, filed Mar. 27, 1987 which is a continuation-in-part patent application of application Ser. No. 838,878 filed Mar. 10, 1986, which in turn is a continuation of application Ser. No. 641,666 filed Aug. 17, 1984.

BACKGROUND OF THE INVENTION

The present invention relates to a new and improved disposable infant diaper. The diaper has improved fit about the waist and the legs of the infant.

Disposable absorbent products have been known for some time including such products as disposable diapers, incontinent pads, and the like. These products incorporate an absorbent batt which is used to absorb and hold or contain body fluids. Initially in many of these products, especially diapers and sanitary napkins, the absorbent batt comprised what is termed wadding or plies of tissue. The wadding was disposed between a liquid-impermeable backing and a liquid-permeable facing and the plies of tissue were used to absorb and hopefully contain the liquid within the product. A diaper which utilizes such an absorbent batt is disclosed in U.S. Reissue Pat. No. 26,151.

The wadding type of product was replaced for the most part by an improved absorbent batt which comprises what is termed "fluffed wood pulp fibers". This absorbent batt comprises a layer of individualized wood pulp fibers with the layer having substantial thickness. A diaper which incorporates such a fluffed wood pulp absorbent batt is described in U.S. Pat. No. 2,788,003. This diaper had improved absorbent capacity and somewhat better containment than a diaper using a wadding layer. Also, the fluffed wood pulp layer is quite soft, flexible, and conformable, and hence produces an improved diaper over diapers using wadding as the absorbent layer. Though the fluffed wood pulp absorbent batt have improved capacity diaper designs, whether they be for the infant or the adult, have followed the standard pattern of having large areas of liquid-impermeable film encompassing the torso.

When the diaper is dry, the wood pulp fluff permits the diaper to breathe to some extent. However, once the diaper is wet and the wood pulp fluff has compacted, the breathability of the diaper reaches a very low point.

Other efforts have been made to conform the diaper about the legs of the wearer to prevent leakage. Though these diapers provide no better absorbent batt than flat diapers of the prior art diapers, they have indicated improved containment of liquid. Such diapers are disclosed and described in U.S. Pat. Nos. 3,860,003; 4,050,462; and 4,324,245. The elasticized produces fit more tightly permitting less air circulation. Frequently, this can become irritating to the skin and the tighter the elastic or the more close fitting the diaper, the greater the irritation. This is especially true adjacent the area where the elastic leg portion of the product contacts the wearer.

The present invention provides a new and improved disposable infant diaper product whose constituency and design is specifically for an infant. This new diaper product absorbs as much urine with less leakage as present commercial diapers, and the wearer experiences less skin irritation than with previously known products.

SUMMARY OF THE INVENTION

The present invention provides a disposable diaper product suitable for use on an infant. The product shape is of a modified "T" configuration and comprises a substantially rectangular absorbent core. The core has a substantially rectangular absorbent panel on one side of which is a liquid barrier, the latter of which is either integral with the panel or is substantially the same shape as the panel but extends slightly beyond each edge of the panel. The absorbent core forms the stem of the "T" and extends substantially the entire length of the diaper product. A first breathable fabric preferably liquid-impermeable, forms the top of the "T" and extends along the stem of the "T" beyond the stem and is placed on the outerside of the liquid barrier. The breathable fabric extends beyond the liquid barrier sufficiently to form margins. A second breathable fabric which is liquid-permeable, covers the absorbent core and extends beyond the core at least sufficiently to be adhered to the first breathable fabric in the margins. The second breathable fabric may be extended to cover other portions of the "T" shape, as desired.

An elastic gathering means is secured between the first and second breathable fabrics in the margins along the stem of the "T" in at least the central portion thereof. Closure means are provided on the inside of each terminating end of the top of the "T" so that the closure means is an integral part of the modified "T" shaped product. The "T" configuration is modified by extending portions of at least one of the breathable fabrics at the base of the "T" along a small portion of the stem of the "T" on each side. The extensions are substantially in equal portions on each side. At least the portion of one of the breathbale fabrics that extends across the top of the "T" or is at the base of the "T" is non-yielding in a crosswise direction in the product. This is required to insure that the waist encircling portions of the diaper be non-yielding. Up to about 10 percent yielding at a grab tensile force of 2.5 pounds can be tolerated. By non-yielding is meant that if the fabric is extended it does not remain extended.

It is important that the closure means be disposed on the inside surface of the top of the "T" so that the waistband portion of the diaper has uniform non-extensibility over its entire width.

The combination of the modified "T" configuration and the non-yielding fabrics provides a product which fits the infant's torso securely and yet provides a high degree of breathability. At least about 35 percent and generally more than 40 percent of the diaper product is breathable. Included in the breathable area are the elastics. This modified "T" configuration accommodates a thin absorbent core or a thick absorbent core.

DETAILED DESCRIPTION OF THE INVENTION

Figure 1:
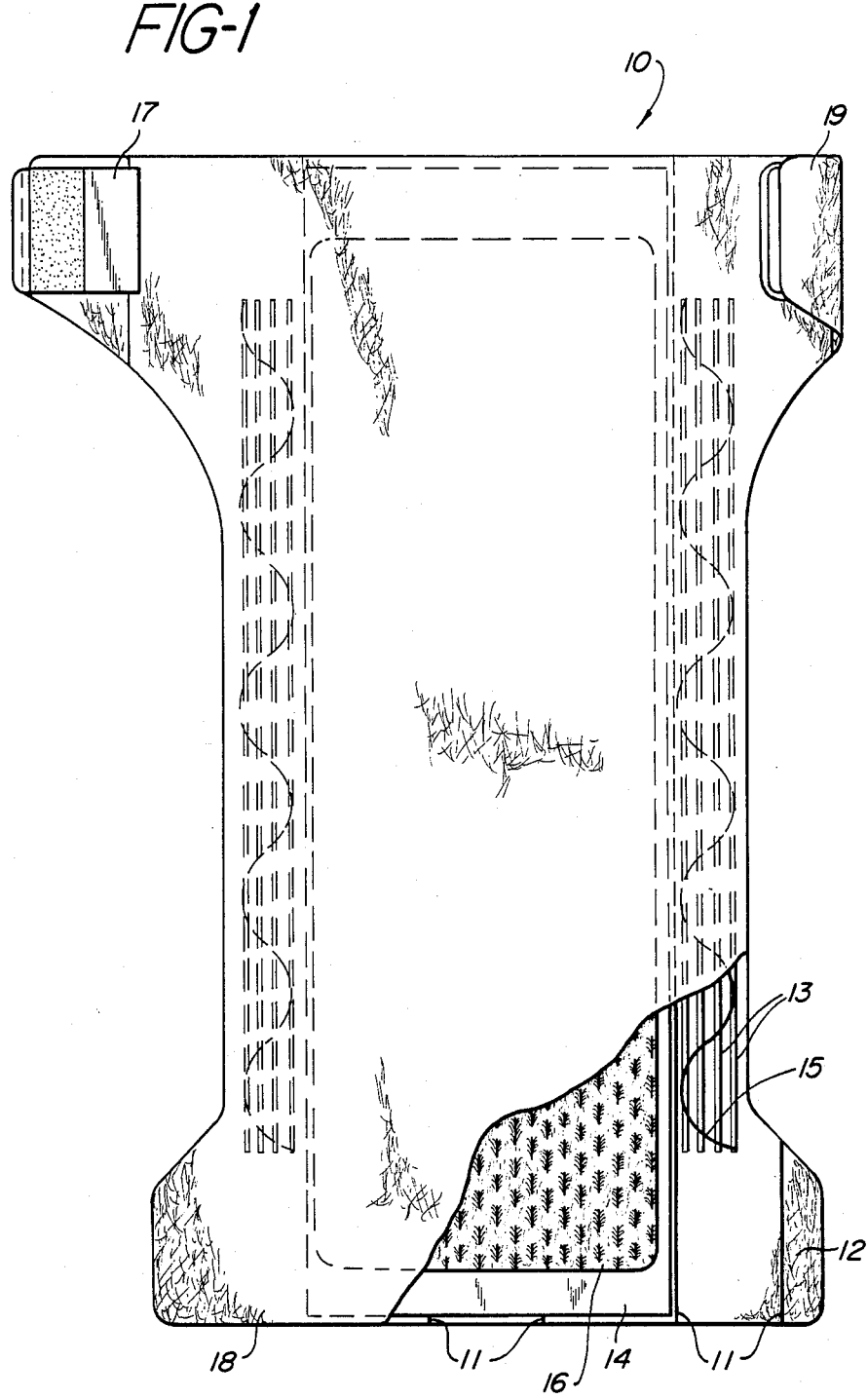
FIG. 1 is a plan view illustrating one embodiment of the present invention.

Referring now to the drawings. FIG. 1 represents a top view of the disposable diaper product of the present invention. The diaper 10 has a spun bonded polypropylene breathable fabric backing 12 which is substantially in the shape of a "T" but modified as discussed hereinafter. A liquid barrier 14, such as a polyethylene film, is of substantially rectangular shape and is placed on the backing 12. The absorbent panel 16 is slightly smaller than the liquid barrier and is placed centrally located on the liquid barrier. Another sheet of polypropylene fabric 18 is placed on top of the product to create the facing which comes in contact with the infant's skin. In the margin, elastic strands 13 are placed alongside the liquid barrier and the absorbent panel. In this embodiment, the elastic means consists of multiple strands of elastic 13 which are adhered by the glue line 15. If desired, a multiplicity of glue lines may be used. The diaper is secured about the body of the infant by the closure means 17 and 19. The closure 17 is shown in its open position ready to apply and closure means 19 is shown in its closed storage position.

Figure 2:
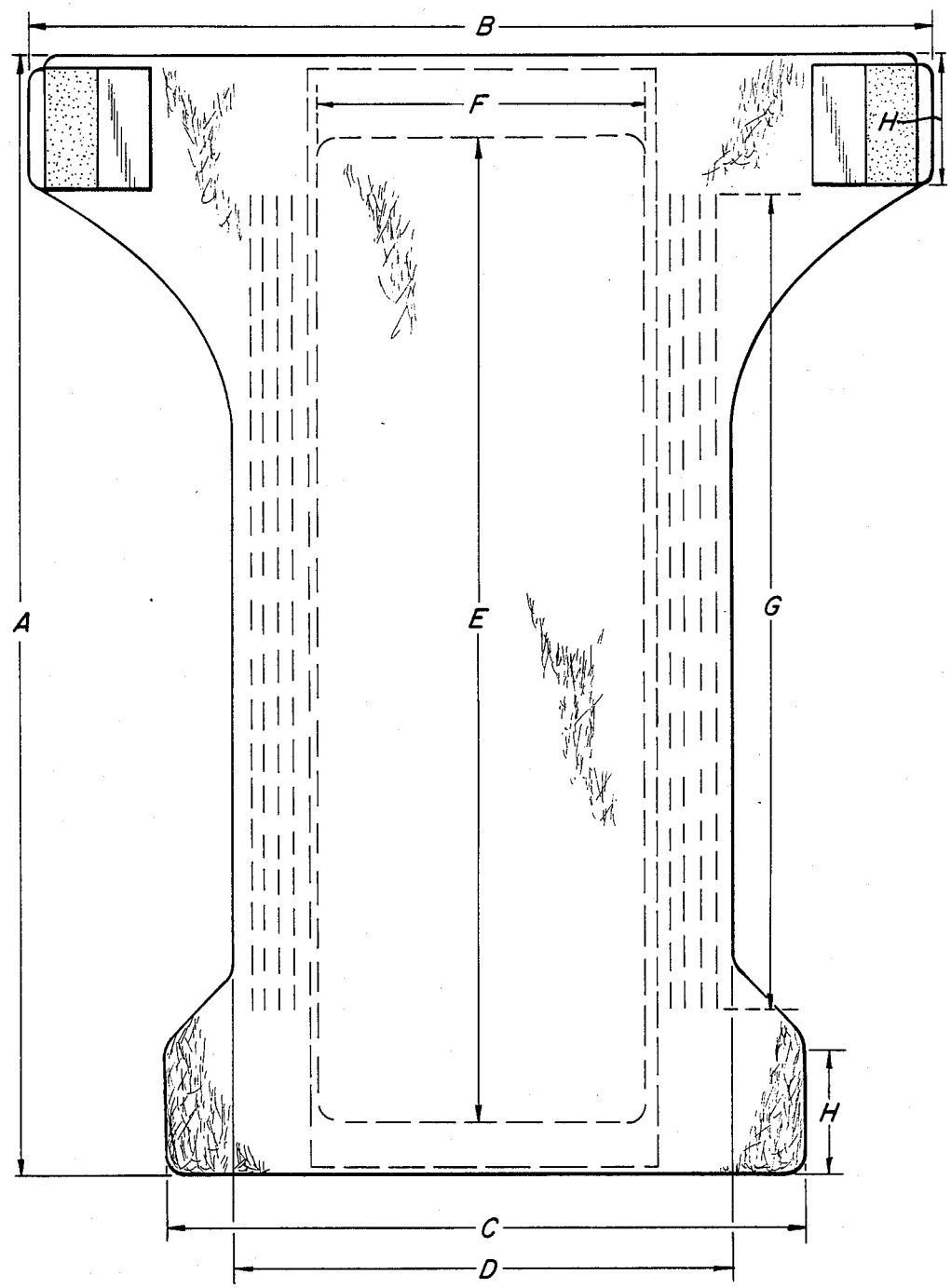
FIG. 2 is a plan view of the embodiment of FIG. 1 with special delineations showing the relationship of parts of the diaper configuration.

FIG. 2 depicts the same diaper but in addition shows the relationship of the measurements of the part of the diaper modified "T" configuration. Assuming that the length of the diaper product A is equal to "x", the width of the back waist portion B is about 0.8x and the width of the front waist portion C is about 0.5x, or slightly more up to 0.55x. The center width D of the product is about 0.45 to 0.51x. The length of the absorbent panel E is about 0.9x, whereas the length of the liquid barrier is substantially equal to x. The width of the absorbent panel F is from about 0.2x to about 0.5x, preferably about 0.25x. The effective elastic length G is about 0.65x. The width of the gathering area of the elastic is at least $\frac{1}{4}$ inch and preferably about $\frac{3}{4}$ to 1 inch. The extension of the diaper at the base of the "T" is equal to the difference in width between the central portion of the diaper and the front waist portion. This difference generally is 0.05x or slightly larger. The length of the top of the "T" H and the extension at the base of the "T" H generally is about 0.1x. The adhesive portion of the closure means extends vertically at least about 0.05x and laterally is about 0.04x or larger. It is important that the vertical adhesion distance be at least about 0.05x and preferably about 0.08x or 0.1x. It is important that the adhesive be on the inside surface of the "T" so that the breathable fabrics act as the backing for the closure and uniform extensibility is attained arms the entire width of the diaper to the waistband portion. It is also important that the line from the edge of the top of the "T" toward the stem is a concave line.

The absorbent core of the product is comprised of an absorbent panel and a liquid barrier, the latter of which may be integral with the panel as a layer sprayed thereon or is a liquid barrier sheet slightly larger in area than the absorbent panel. The absorbent panel may be an absorbent batt of lightly compacted cellulosic fibers, such as wood pulp fibers, or a compressed composite product, or the like. The compressed composite product is described in copending application Ser. No. 439,963 filed Nov. 8, 1982, briefly this product consists of an absorbing layer containing superabsorbent and a wicking layer, such as a layer of wood pulp fibers, which layers are compressed to provide a product resulting in an absorbent product which absorbs large quantities of liquid.

The liquid barrier when it is separate from the panel is generally a liquid-impermeable film such as a polyethylene film. The film is of substantially the same shape as the absorbent panel but is slightly larger than the panel in order to be sure that the underside of the absorbent panel is completely covered by the liquid barrier so as to prevent leakage. When the barrier is integral with the panel, such as a latex layer or the like, it extends over at least one surface of the panel.

The backing and facing are of breathable fabrics, such as a spun bonded polypropylene fabric, a polyester nonwoven fabric, a polypropylene melt blown fabric, and the like. The backing fabric preferably is substantially liquid-impermeable while the facing fabric is, of course, liquid-permeable.

Conventional elastic means may be used although it is preferred that multiple strands of elastic be placed in the margin of the breathable fabric adjacent the liquid barrier or slightly removed from the edge of the liquid barrier. The elastic extends about 65 percent of the length of the product. However, the elastic is not centered in the length but rather extends closer to the end of the diaper at the back waistband than it does to the front. Specifically, the elastic extends about 55 percent above the center transverse axis and 45 percent below, i.e., toward the front waistband. The effective width of the elastic is from about $\frac{1}{4}$ inch to about 1 inch, or more such as $1\frac{1}{2}$ inches. As heretofore mentioned, the elastic can be a single elastic band, a reticulated elastic band, or multiple strands of elastic which are separated at least 1/16 inch one from the other. It has been found that four strands of elastic placed about 3/16 inch apart and laminated between the facing and the backing fabric is particularly suitable.

When the absorbent panel is of the conventional type generally made from loosely compacted cellulosic fibers, such as wood pulp fibers, it is particularly desirable to stabilize the absorbent batt. Generally, the wood pulp fibers are quite short, e.g., $\frac{1}{4}$ inch or less, and are airlaid to form an absorbent batt. The batt may be stabilized by treatment in accordance with U.S. Pat. No. 3,017,304, which incorporates in the absorbent batt a densified paper-like layer. This paper-like layer acts as a wick i.e., liquid which is placed on the layer tends to move rapidly along the plane of the layer. When incorporated in combination with fluffed wood pulp fiber, the resultant product uses the absorbent capacity of the fluffed wood pulp much more efficiently. Other cellulosic fibers that might be used in an absorbent batt are rayon fibers, flax, hemp, jute, ramie, cotton, cotton linters, and the like. U.S. Pat. Nos. 3,612,055 and 3,938,522 incorporate not only the paper-like layer in a wood pulp fiber batt but also place embossed lines into the batt.

An example of the disposable diaper product of the present invention is as follows. This example is not intended to be limiting in any way and extensions and modifications thereof without departure from the spirit and scope of the invention will become apparent from the example.

EXAMPLE

An absorbent panel is formed having a length of 16 inches and a width of 4.5 inches. The panel is a compressed composite heretofore mentioned. A liquid barrier sheet which is 17.75 inches long and 6.25 inches wide is placed under the panel. The backing sheet is a spun bonded polypropylene, breathable, substantially liquid-impermeable, nonwoven fabric, which has a length of 17.75 inches and a width at the back waistband of 14.5 inches. The width at the front waistband is 9.5 inches and in the center is 8.5 inches. Four strands of elastic about $\frac{1}{8}$ inch apart, each of which is 11.5 inches long, are placed in the side margin on each side of the absorbent core. The elastic is originally 8⅜ inches long and is stretched to 11.5 inches and the 11.5 inch length is glued to the backing sheet. The elastic is placed so that 6.25 inches of the elastic are in the back half of the leg encircling portion of the diaper which forms the back waistband and 5.25 inches are in the front half of the diaper. This placement of the elastic forms a soft, but complete, seal about the leg of the infant. A facing also of spun bonded polypropylene, nonwoven fabric is cut to substantially the same shape as the backing and is adhered in the margins to the backing. Integral adhesive closure means are affixed to the diaper ears at the back waistband. The closure means is an adhesive tape repositionable closure. In other words, the diaper may be taken on and off several times using the same tape closure means.

The finished product when placed on an infant does not stretch at the waist because the materials used for the breathable fabric are those which will not yield more than about 10 percent. The improvement in the seal about the leg of the infant is substantial in that the gasketing is very gentle, yet is substantially complete. This is provided by the placement of the multiple strands of elastic giving more elastic gathering toward the back of the diaper than the front as well as the use of the multiple strands of elastic which each provide its own line of gasketing. Furthermore, the modified "T" configuration of the product as shown in FIGS. 1 and 2 provides a configuration which, whether the absorbent core is thick or thin, fits an infant's torso and legs very well.

The disposable diaper made in accordance with the present invention affords many advantages. Because the product fits the infant, the clothing placed over the diaper fits much better. The breathability of the backing and facing fabrics reduces incidents of skin irritation. Also the soft gathering provided by elastic effective over a width of at least ½ inch, reduces irritation to the skin. The all fabric backing and facing prevents perspiration on the arm of one carrying the infant. Other advantages of the product include reduced leakage and improved comfort.

From the foregoing it will be observed that numerous variations and modifications may be effected without departing from the true spirit and scope of the novel concept of this invention.

We claim:

1. A disposable infant diaper having a modified "T" configuration comprising:

(a) a substantially rectangular absorbent core, said core comprising a substantially rectangular absorbent panel superimposed on a liquid barrier, said barrier being substantially the same shape as said panel but extending slightly beyond each edge of said panel, said core forming the stem of the "T" and extending substantially the entire length of the "T";

(b) a first breathable fabric underlying the absorbent panel and liquid barrier and forming the top of the "T" and extending beyond the stem of the "T" to form margins, said first breathable fabric being vapor permeable but liquid impermeable;

(c) a second breathable fabric covering said absorbent core and extending beyond said core at least sufficiently to be adhered to said first breathable fabric in the margins, said second breathable fabric being both liquid and vapor permeable;

(d) at least one of said breathable fabrics extending beyond the edges of the absorbent core at the base of the "T" in substantially equal portions, said extensions at the base of the "T" being substantially less than the extensions of the first breathable fabric at the top of the "T";

(e) elastic gathering means secured between said first and second breathable fabrics in said margin along the stem of the "T" at least in the central portion thereof;

(f) closure means attached on the inside of each terminating end of the top of the "T", both of said breathable fabrics being substantially nonextendable in a crosswise direction; and (g) said disposable diaper having dimensions wherein the length of the "T" configuration A is x, the width across the top of the "T" B is about 0.8x, the width of the base of the stem of the "T" C is from about 0.5x to about 0.55x, the width of the stem of the "T" D at the transverse axis at the center of the length of the product is from about 0.45x to about 0.50x, the length of the panel E is about 0.9x, the width of the panel F is about 0.25x, the length of the elastic is about 0.65x, said elastic length being distributed about 55 percent above the transverse axis and about 45 percent below the transverse axis, and said elastic width being at least about 0.5 inch, and said closure longitudinal length I is at least about 0.08x and the terminating ends of the top of the "T" H are about 0.1x.

* * * * *